(12) United States Patent
Garner

(10) Patent No.: US 12,385,896 B2
(45) Date of Patent: Aug. 12, 2025

(54) TRANSPORTING CLASTIC ROCK SAMPLES FOR PALYNOMORPH ANALYSIS

(71) Applicant: Saudi Arabian Oil Company, Dhahran (SA)

(72) Inventor: Nicoli Albert Garner, Newark, DE (US)

(73) Assignee: Saudi Arabian Oil Company, Dhahran (SA)

( * ) Notice: Subject to any disclaimer, the term of this patent is extended or adjusted under 35 U.S.C. 154(b) by 833 days.

(21) Appl. No.: 17/683,739

(22) Filed: Mar. 1, 2022

(65) Prior Publication Data

US 2023/0280327 A1    Sep. 7, 2023

(51) Int. Cl.
*G01N 33/24* (2006.01)
*B64U 10/13* (2023.01)
(Continued)

(52) U.S. Cl.
CPC ........... *G01N 33/24* (2013.01); *G01N 1/4044* (2013.01); *B64U 10/13* (2023.01); *B64U 2101/60* (2023.01); *G01N 2001/005* (2013.01)

(58) Field of Classification Search
CPC ............... G01N 33/24; G01N 1/4044; G01N 2001/005; B64U 10/13; B64U 2101/60;
(Continued)

(56) References Cited

U.S. PATENT DOCUMENTS 5,098,844 A * 3/1992 Royle .................... G01N 33/24
436/31
5,135,871 A * 8/1992 Colling, Jr. .............. G01N 1/40
436/178
2019/0264132 A1    8/2019 Nates et al.

FOREIGN PATENT DOCUMENTS

| CN | 203732334 | 7/2014 |
| GB | 2408008 | 5/2005 |

(Continued)

OTHER PUBLICATIONS

Batten et al., "Methods of palynological preparation for palaeoenvironmental, source potential and organic maturation studies," Norwegian Petroleum Directorate Bulletin, 1998, 2:35-53, 19 pages.

(Continued)

*Primary Examiner* — Dennis White
(74) *Attorney, Agent, or Firm* — Fish & Richardson P.C.

(57) ABSTRACT

An apparatus for transporting a clastic rock sample including a palynomorph includes a housing, a reaction vessel, multiple rods, a lid, a pressure release tubing, and a spill neutralization padding. The reaction vessel is disposed within the housing. The reaction vessel is configured to hold a specified quantity of hydrofluoric acid and the clastic rock sample. The rods extend from the housing to the reaction vessel. The lid is configured to seal against the reaction vessel to isolate an inner volume of the reaction vessel from an external environment. The pressure release tubing is configured to couple to a pressure relief valve and establish fluid communication between the annular volume and the pressure relief valve. The spill neutralization padding is configured to react with the hydrofluoric acid in an acid-base neutralization reaction in response to coming in contact with the hydrofluoric acid.

19 Claims, 5 Drawing Sheets

(51) Int. Cl.
  *B64U 101/60*  (2023.01)
  *G01N 1/00*   (2006.01)
  *G01N 1/40*   (2006.01)

(58) Field of Classification Search
  CPC .......... B01L 3/50825; B01L 2200/082; B01L 2200/085; B01L 2200/185; B01L 2300/043; B01L 2300/048; B01L 2300/049; B64C 39/024; B64C 27/20
  See application file for complete search history.

(56) References Cited

FOREIGN PATENT DOCUMENTS

| WO | WO 1995022761 | 8/1995 | |
| WO | WO-9625652 A2 * | 8/1996 | ............... C09K 8/74 |

OTHER PUBLICATIONS

Batten, "Palynofacies and palaeoenvironmental interpretation," In Jansonius, J., and D.C. McGregor (eds.), Palynology: principles and applications, American Association of Stratigraphic Palynologists Foundation, 1996, Chapter 26A, 1011-1064, 55 pages.

emergenresearch.com [online], "Top 10 Companies in the Drone Package Delivery Industry," Apr. 2022, retrieved Apr. 21, 2022, retrieved from URL <https://www.emergenresearch.com/blog/top-10-companies-in-the-drone-package-delivery-industry>, 5 pages.

Riding et al., "A direct comparison of three palynological preparation techniques," Review of Palaeobotany and Palynology, 2011, 167:212-221, 10 pages.

Riding et al., "An Effective Palynological Preparation Procedure Using Hydrogen Peroxide," Palynology, 2007, 31(1):19-36, 27 pages.

savillex.com [online], "Savillex Digestion Vessel Dimensions," retrieved Apr. 21, 2022, retrieved from URL <https://www.savillex.com/Image/GetDocument/en/33/digestion%20vessels%20specifications.PDF>, 1 page.

savillex.com [online], "Savillex Digestion Vessel, 120 mL Digestion Vessel, Flat Interior, Flat Exterior, Buttress Threaded Top," 2016-2022, retrieved Apr. 21, 2022, retrieved from URL <https://www.savillex.com/en/product/digestion-vessels/120-ml-digestion-vessel-flat-interior-flat-exterior-buttress-threaded-top--300-120-03?pageid=19>, 3 pages.

Wood et al., "Palynological techniques—processing and microscopy," In Palynology: principles and applications, Jansonius J, McGregor DC (ed.), American Association of Stratigraphic Palynologists Foundation, 1996, Chapter 3, 29-50, 22 pages.

* cited by examiner

TRANSPORTING CLASTIC ROCK SAMPLES FOR PALYNOMORPH ANALYSIS

TECHNICAL FIELD

This disclosure relates to transporting clastic rock samples, and in particular, transporting the rock samples for palynomorph analysis.

BACKGROUND

Sedimentary rocks are formed by the deposition of geological and biological materials. Captured in a sediment sequence can be various amounts of acritarch, chitinozoan, pollen, spore, and other organic matter. When preserved in sediment, these are known as fossil palynomorphs. The abundance and distribution through geological time form assemblages known as palynofacies. Fossil palynofacies data can be evaluated and interpreted to provide a chronostratigraphic framework, along with paleoenvironmental and paleoclimatological information. Palynomorph analysis can improve the understanding of time-stratigraphy, paleogeographical, and paleoclimatological relationships enhancing the prediction of reservoir distribution.

SUMMARY

This disclosure describes technologies relating to transporting clastic rock samples, and in particular, transporting the rock samples for palynomorph analysis via hydrofluoric acid maceration. Certain aspects of the subject matter described can be implemented as an apparatus for transporting a clastic rock sample that includes a palynomorph. The apparatus includes a housing, a reaction vessel, multiple rods, a lid, a pressure release tubing, and a spill neutralization padding. The reaction vessel is disposed within the housing. The reaction vessel is configured to hold a specified quantity of hydrofluoric acid and the clastic rock sample. The rods are disposed within the housing. Each of the rods extend from the housing to the reaction vessel. The rods secure a position of the reaction vessel within the housing. The lid is configured to seal against the housing to isolate an annular volume between the housing and the reaction vessel from an external environment. The lid is configured to seal against the reaction vessel to isolate an inner volume of the reaction vessel from the external environment. The pressure release tubing extends through the lid. The pressure release tubing is configured to couple to a pressure relief valve and establish fluid communication between the annular volume and the pressure relief valve once the pressure relief valve is coupled to the pressure release tubing and the lid has sealed against the housing and the reaction vessel. The spill neutralization padding surrounds an external surface of the housing. The spill neutralization padding is configured to react with the hydrofluoric acid in an acid-base neutralization reaction in response to coming in contact with the hydrofluoric acid.

This, and other aspects, can include one or more of the following features. The lid can be attached to the housing by a hinge. The hinge can be configured to swing the lid between a closed position and an open position. In the open position, the inner volume of the reaction vessel can be open for receiving the specified quantity of hydrofluoric acid and the clastic rock sample. In the closed position, the lid can be sealed against the housing and the reaction vessel, thereby isolating the annular volume and the inner volume from the external environment. Each of the rods can extend radially outward from an outer circumferential wall of the reaction vessel to an inner circumferential wall of the housing. A volumetric ratio of the annular volume between the housing and the reaction vessel to the inner volume of the reaction vessel can be in a range of from 2:1 to 15:1. The spill neutralization padding can include calcium carbonate. A ratio of a thickness of the spill neutralization padding to an inner diameter of the reaction vessel can be about 8:1.

Certain aspects of the subject matter described can be implemented as a method for transporting a clastic rock sample that includes a palynomorph. At a well site, the clastic rock sample is placed in an apparatus. The apparatus includes a housing, a reaction vessel, multiple rods, a lid, a pressure release tubing, and a spill neutralization padding. The reaction vessel is disposed within the housing. The rods are disposed within the housing. Each of the rods extend from the housing to the reaction vessel. The rods secure a position of the reaction vessel within the housing. The lid is configured to seal against the housing to isolate an annular volume between the housing and the reaction vessel from an external environment. The lid is configured to seal against the reaction vessel to isolate an inner volume of the reaction vessel from the external environment. The pressure release tubing extends through the lid. The pressure release tubing is configured to couple to a pressure relief valve and establish fluid communication between the annular volume and the pressure relief valve once the pressure relief valve is coupled to the pressure release tubing and the lid has sealed against the housing and the reaction vessel. The spill neutralization padding surrounds an external surface of the housing. The spill neutralization padding is configured to react with the hydrofluoric acid in an acid-base neutralization reaction in response to coming in contact with the hydrofluoric acid. Placing the clastic rock sample in the apparatus includes placing the clastic rock sample within the inner volume of the reaction vessel. After placing the clastic rock sample within the inner volume of the reaction vessel, hydrofluoric acid is placed within the inner volume of the reaction vessel. The pressure relief valve is coupled to the pressure release tubing. The lid is sealed against the housing and the reaction vessel, thereby isolating the hydrofluoric acid and the clastic rock sample within the inner volume of the reaction vessel. The apparatus is transported away from the well site.

This, and other aspects, can include one or more of the following features. Transporting the apparatus away from the well site can include placing the apparatus on an unmanned aerial vehicle (UAV) and causing the UAV to transport the apparatus away from the well site to a laboratory. The lid can be attached to the housing by a hinge. The hinge can allow the lid to swing between a closed position and an open position. In the open position, the inner volume of the reaction vessel can be open for receiving the clastic rock sample and the hydrofluoric acid. In the closed position, the lid can be sealed against the housing and the reaction vessel, thereby isolating the annular volume and the inner volume from the external environment. The lid can seal against the housing and the reaction vessel by swinging the lid to the closed position. Each of the rods can extend radially outward from an outer circumferential wall of the reaction vessel to an inner circumferential wall of the housing. A volumetric ratio of the annular volume between the housing and the reaction vessel to the inner volume of the reaction vessel can be in a range of from 2:1 to 15:1. The spill neutralization padding can include calcium carbonate. A ratio of a thickness of the spill neutralization padding to an inner diameter of the reaction vessel can be about 8:1.

The clastic rock sample can include a mixture of rock cuttings and at least a portion of a crushed core sample. Placing the hydrofluoric acid in the inner volume of the reaction vessel can include placing about 25 milliliters (mL) to about 60 mL of a 48% hydrofluoric acid solution in the inner volume of the reaction vessel. Hydrofluoric acid can be added to the clastic rock sample prior to placing the clastic rock sample within the inner volume of the reaction vessel. After transporting the apparatus away from the well site, the lid can be unsealed from the housing and the reaction vessel. After transporting the apparatus away from the well site, the hydrofluoric acid can be removed from the reaction vessel. After transporting the apparatus away from the well site, the clastic rock sample within the reaction vessel can be neutralized. Neutralizing the clastic rock sample can include: a) placing distilled water in the reaction vessel; b) allowing the clastic rock sample to rest in the distilled water for a specified resting time duration; c) removing the distilled water from the reaction vessel; and d) repeating in order a), b), and c) for example, two times, three times, or at least three times.

Certain aspects of the subject matter described can be implemented as a system. The system includes a clastic rock sample and an apparatus for transporting the clastic rock sample. The clastic rock sample includes a palynomorph. The apparatus is configured to be placed on and transported by an unmanned UAV. The apparatus includes a housing, a reaction vessel, multiple rods, a lid, a hinge, a pressure release tubing, a pressure relief valve, and a spill neutralization padding. The reaction vessel is disposed within the housing. The reaction vessel is configured to hold a specified quantity of hydrofluoric acid and the clastic rock sample. The rods are disposed within the housing. Each of the rods extend from the housing to the reaction vessel. The rods secure a position of the reaction vessel within the housing. The lid is configured to seal against the housing to isolate an annular volume between the housing and the reaction vessel from an external environment. The lid is configured to seal against the reaction vessel to isolate an inner volume of the reaction vessel from the external environment. The hinge attaches the lid to the housing. The hinge is configured to swing the lid between a closed position and an open position. In the open position, the inner volume of the reaction vessel is open for receiving the specified quantity of hydrofluoric acid and the clastic rock sample. In the closed position, the lid is sealed against the housing and the reaction vessel, thereby isolating the annular volume and the inner volume from the external environment. The pressure release tubing extends through the lid. The pressure relief valve is coupled to the pressure release tubing. The pressure release tubing is configured to establish fluid communication between the annular volume and the pressure relief valve once the pressure relief valve is coupled to the pressure release tubing and the lid has sealed against the housing and the reaction vessel. The pressure relief valve is configured to relieve pressure from the annular volume once a pressure within the annular volume has reached a maximum threshold pressure value. The spill neutralization padding surrounds an external surface of the housing. The spill neutralization padding is configured to react with the hydrofluoric acid in an acid-base neutralization reaction in response to coming in contact with the hydrofluoric acid.

This, and other aspects can include one or more of the following features. A volumetric ratio of the annular volume between the housing and the reaction vessel to the inner volume of the reaction vessel can be in range of from 2:1 to 15:1. The spill neutralization padding can include calcium carbonate. A ratio of a thickness of the spill neutralization padding to an inner diameter of the reaction vessel can be about 8:1. The clastic rock sample can include a mixture of rock cuttings and at least a portion of a crushed core sample.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes transport of clastic rock samples, and in particular, transport of the rock samples for palynomorph analysis via hydrofluoric acid maceration. The apparatus includes a hydrofluoric acid maceration vessel. A clastic rock sample is placed in the vessel, and hydrofluoric acid is added to begin the hydrofluoric acid maceration process. The hydrofluoric acid maceration process is implemented to concentrate and isolate the organic matter in the rock sample. Hydrofluoric acid reacts with rock materials (for example, silicates) while leaving the organic matter largely unaltered for subsequent evaluation. As described herein, the apparatus includes various safety measures to ensure safe and reliable transport of the sample (along with hydrofluoric acid), such that the hydrofluoric acid maceration process can occur during transport, which can greatly reduce sample preparation time at a laboratory, where the sample is analyzed, for example, to determine thermal maturity of the organic content in the source rock.

The subject matter described in this disclosure can be implemented in particular implementations, so as to realize one or more of the following advantages. The apparatuses and methods described can be implemented to transport clastic rock samples that include palynomorphs in a safe and reliable manner. The apparatuses described can be placed on and transported by unmanned vehicles (for example, unmanned aerial vehicles) from well sites to laboratories, so that the samples can be analyzed. By utilizing unmanned vehicles, the apparatuses and methods described can mitigate/eliminate the need for technicians to travel to remote locations to transport samples for analysis, which can, in turn, mitigate/eliminate vehicular accidents and improve cost efficiency. The apparatuses and methods described can be implemented to safely transport clastic rock samples that have been pre-treated with hydrofluoric acid, which can significantly reduce sample preparation time in the laboratory. The methods described can be scaled to accommodate periods of rapid drilling (that is, rate of penetration into a subterranean formation), especially in cases where sample availability is greater than transportation capacities. In some cases, the apparatuses and methods described can implement ballistic/projectile transportation.

Figure 1:
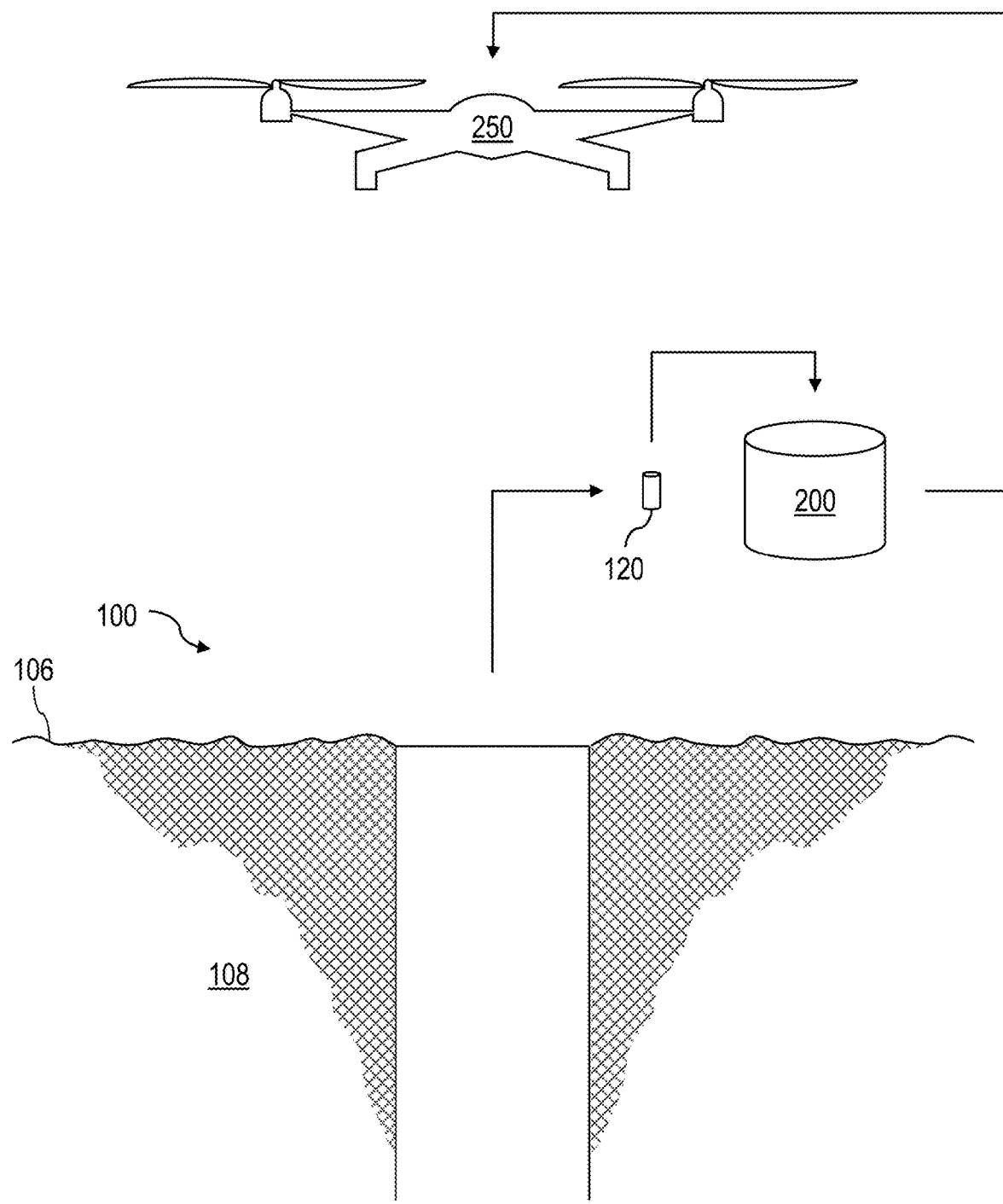
FIG. 1 is a schematic diagram of an example well.

FIG. 1 depicts an example well 100 constructed in accordance with the concepts herein. The well 100 extends from the surface 106 through the Earth 108 to one or more subterranean zones of interest. The well 100 enables access to the subterranean zones of interest to allow recovery (that is, production) of fluids to the surface 106 and, in some implementations, additionally or alternatively allows fluids to be placed in the Earth 108. In some implementations, the subterranean zone is a formation within the Earth 108 defining a reservoir, but in other instances, the zone can be multiple formations or a portion of a formation. The subterranean zone can include, for example, a formation, a portion of a formation, or multiple formations in a hydrocarbon-bearing reservoir from which recovery operations can be practiced to recover trapped hydrocarbons. In some implementations, the subterranean zone includes an underground formation of naturally fractured or porous rock containing hydrocarbons (for example, oil, gas, or both). In some implementations, the well can intersect other types of formations, including reservoirs that are not naturally fractured. For simplicity's sake, the well 100 is shown as a vertical well, but in other instances, the well 100 can be a deviated well with a wellbore deviated from vertical (for example, horizontal or slanted), the well 100 can include multiple bores forming a multilateral well (that is, a well having multiple lateral wells branching off another well or wells), or both.

In some implementations, the well 100 is a gas well that is used in producing hydrocarbon gas (such as natural gas) from the subterranean zones of interest to the surface 106. While termed a "gas well," the well need not produce only dry gas, and may incidentally or in much smaller quantities, produce liquid including oil, water, or both. In some implementations, the well 100 is an oil well that is used in producing hydrocarbon liquid (such as crude oil) from the subterranean zones of interest to the surface 106. While termed an "oil well," the well not need produce only hydrocarbon liquid, and may incidentally or in much smaller quantities, produce gas, water, or both. In some implementations, the production from the well 100 can be multiphase in any ratio. In some implementations, the production from the well 100 can produce mostly or entirely liquid at certain times and mostly or entirely gas at other times. For example, in certain types of wells it is common to produce water for a period of time to gain access to the gas in the subterranean zone. The concepts herein, though, are not limited in applicability to gas wells, oil wells, or even production wells, and could be used in wells for producing other gas or liquid resources or could be used in injection wells, disposal wells, or other types of wells used in placing fluids into the Earth.

A clastic rock sample 120 can be obtained from the well 100. The rock sample 120 includes a palynomorph. A palynomorph is an organic-walled microfossil. The palynomorph can, for example, have a size in a range of from about 5 micrometers to about 500 micrometers. The rock sample 120 includes rock cuttings, a core sample, a crushed core sample, or any combination of these. The rock sample 120 can be placed in an apparatus 200 for safely transporting the rock sample 120. Once the rock sample 120 has been placed in the apparatus 200, the apparatus 200 (and rock sample 120) can be transported away from the well site. The apparatus 200 can be transported away from the well site using a vehicle 250. The vehicle 250 can be, for example, an unmanned aerial vehicle (UAV), an unmanned ground vehicle (UGV), or an unmanned surface vehicle (USV), such as an unmanned marine vehicle (UMV) or an unmanned underwater vehicle (UUV).

Figure 2A:
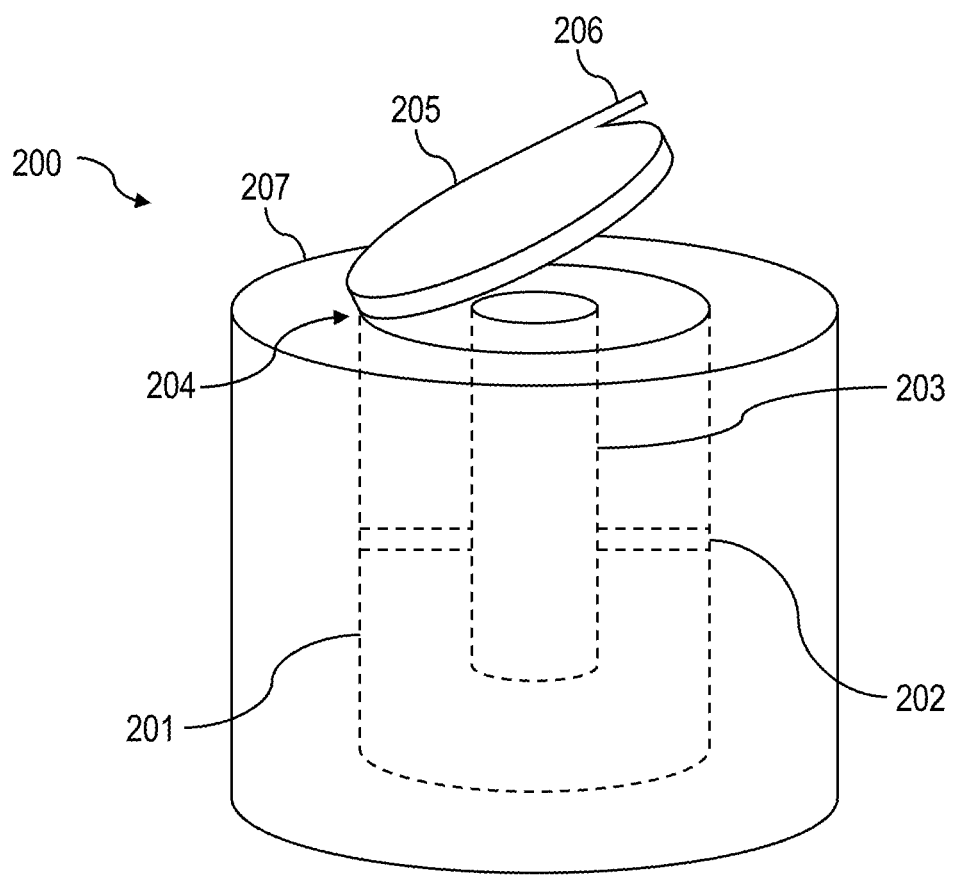
FIG. 2A is a perspective view of an example apparatus for transporting a rock sample.

FIG. 2A depicts an implementation of the apparatus 200, which can be used to transport the rock sample 120. The apparatus 200 includes a housing 201, a reaction vessel 203, a lid 205, and a spill neutralization padding 207. The reaction vessel 203 is disposed within the housing 201 and is configured to hold a specified quantity of hydrofluoric acid and the rock sample 120 during transport. The apparatus 200 includes rods 202 disposed within the housing 201. Each of the rods 202 extend from the housing 201 to the reaction vessel 203. The rods 202 secure a position of the reaction vessel 203 within the housing 201. The lid 205 is configured to seal against the housing 201 to isolate an annular volume between the housing 201 and the reaction vessel 203 from an external environment. The lid 205 is configured to seal against the reaction vessel 203 to isolate an inner volume of the reaction vessel 203 from the external environment. This lid 205 is made of a material that is inert to (that is, does not react with) the hydrofluoric acid. In some implementations, the lid 205 and the housing 201 can be threadedly coupled together. In some implementations, the lid 205 is coupled to the housing 201 by a hinge 204, and the lid 205 is a self-sealing lid that forms a seal with the housing 201 in a closed position. The apparatus 200 includes a pressure release tubing 206 that extends through the lid 205. The pressure release tubing 206 is configured to couple to a pressure relief valve 208. Once the pressure relief valve 208 is coupled to the pressure release tubing 206 and the lid 205 has sealed against the housing 201 and the reaction vessel 203, the pressure release tubing 206 establishes fluid communication between the annular volume and the pressure relief valve 208. The spill neutralization padding 207 surrounds an external surface of the housing 201. The spill neutralization padding 207 is configured to, in response to coming in contact with hydrofluoric acid, react with the hydrofluoric acid in an acid-base neutralization reaction. The spill neutralization padding 207 can be made of an alkaline material. For example, the spill neutralization padding 207 can include calcium carbonate, calcium oxide, calcium hydroxide, calcium gluconate, benzalkonium chloride, or any combination of these.

Figure 2B:
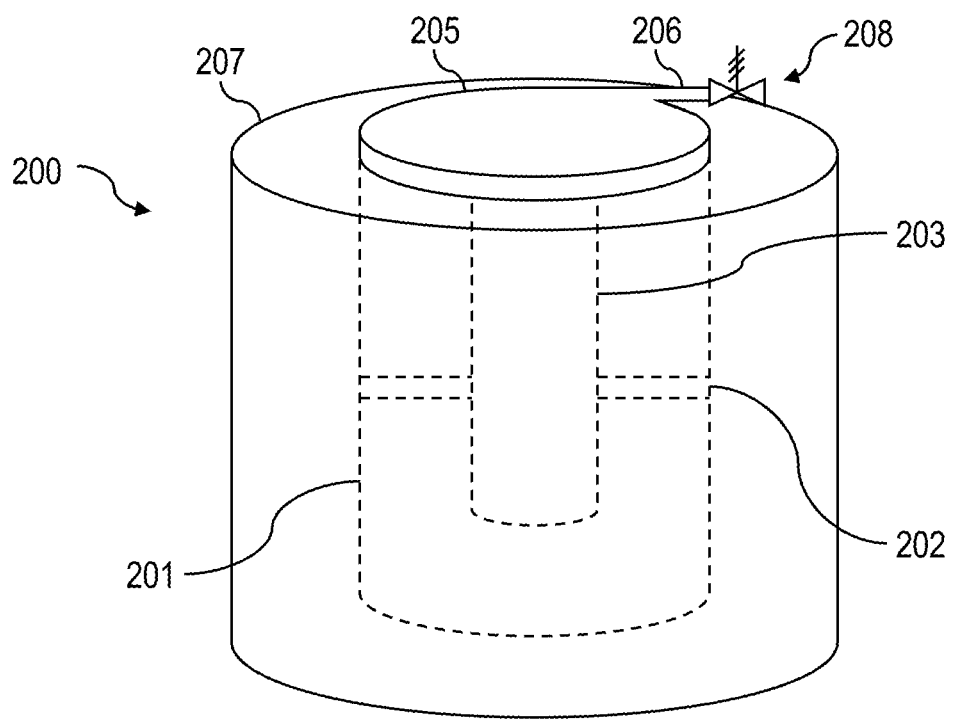
FIG. 2B is a perspective view of the apparatus of FIG. 2A in a closed position.
Figure 2C:
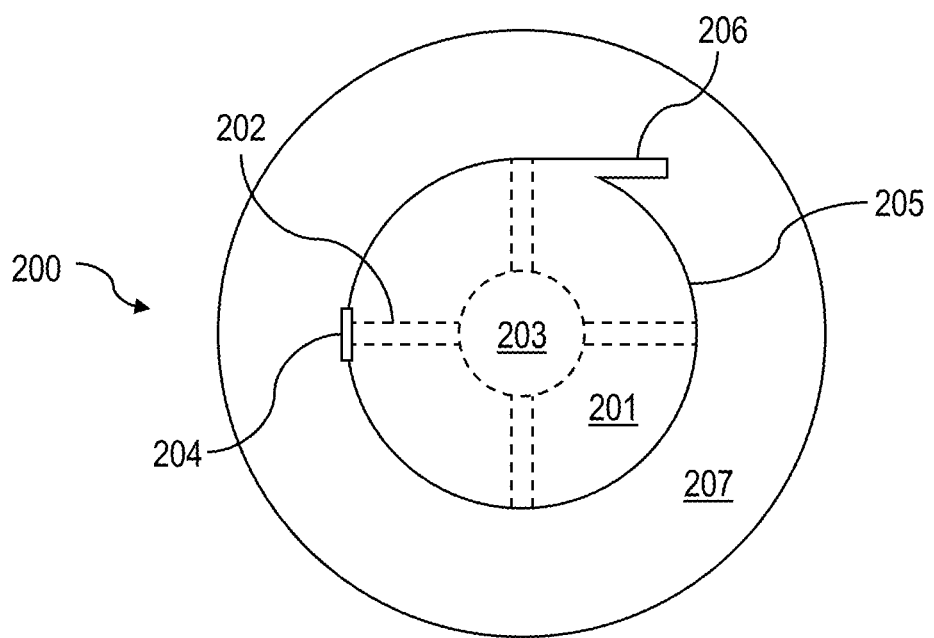
FIG. 2C is a top view of the apparatus of FIG. 2A, showing inner components.

The apparatus 200 can include a hinge 204 that attaches the lid 205 to the housing 201. The hinge 204 allows the lid 205 to swing between a closed position and an open position. In FIG. 2A, the lid 205 is shown in the open position. In the open position, the inner volume of the reaction vessel 203 is open for receiving the specified quantity of hydrofluoric acid and the rock sample 120. In FIGS. 2B and 2C, the lid 205 is shown in the closed position. In the closed position, the lid 205 is sealed against the housing 201 and the reaction vessel 203, thereby isolating the annular volume and the inner volume from the external environment. In some implementations, the apparatus 200 includes a latch (not shown) that can be locked to secure the lid 205 in the closed position, for example, during transport.

The housing 201, the reactor vessel 203, the lid 205, and the pressure release tubing 206 are made of a material that is inert to (that is, does not react with) the hydrofluoric acid. Examples of suitable inert materials include polytetrafluoroethylene (Teflon), polyethylene, a fluoropolymer, lead, or platinum. The annular volume provided by the housing 201 acts as a first layer of protection against an uncontrolled release of hydrofluoric acid. For example, if hydrofluoric acid leaks or overflows out of the reaction vessel 203 through a physical defect in the reaction vessel 203, a leak in the seal between the lid 205 and the reaction vessel 203, or any combination of these, the hydrofluoric acid can accumulate in the annular volume. The pressure relief valve 208 and the spill neutralization padding 207 cooperate to act as a second layer of protection against an uncontrolled release of hydrofluoric acid. The pressure relief valve 208 is configured to relieve pressure from the annular volume once a pressure within the annular volume has reached a maximum threshold pressure value. The pressure relief valve 208 relieves pressure, such that rupturing of the housing 201 due to overpressure can be prevented. For example, if hydrofluoric acid leaks or overflows out of the housing 201 through the pressure relief valve 208, a physical defect in the housing 201, a physical defect in the lid 205, a leak in the seal between the lid 205 and the housing 201, or any combination of these, the hydrofluoric acid can come into contact with the spill neutralization padding 207 and react with the spill neutralization padding 207. The acid-base neutralization reaction between the hydrofluoric acid and the spill neutralization padding 207 neutralizes the hydrofluoric acid and mitigates and/or eliminates the negative effects of the uncontrolled release of the hydrofluoric acid.

In some implementations, each of the rods 202 extend radially outward from an outer circumferential wall of the reaction vessel 203 to an inner circumferential wall of the housing 201. Although shown in FIG. 2C as including four rods 202, the apparatus 200 can include fewer than four rods 202 (for example, two rods or three rods) or more than four rods 202 (for example, five rods or more than five rods).

A ratio of an inner diameter of the reaction vessel 203 to an inner diameter of the housing 201 can be in a range of from about 1:2 to about 1:4. For example, the ratio of the inner diameter of the reaction vessel 203 to the inner diameter of the housing 201 can be about 1:3. A ratio of a height of the reaction vessel 203 to a height of the housing 201 can be in a range of from about 1:2 to about 1:1. For example, the ratio of the height of the reaction vessel 203 to the height of the housing 201 can be about 2:3. A volumetric ratio of the annular volume (between the housing 201 and the reaction vessel 203) to the inner volume of the reaction vessel 203 can be in a range of from about 2:1 to about 15:1. For example, the ratio of the annular volume to the inner volume of the reaction vessel 203 can be about 4:1. In some implementations, the housing 201 has a total inner volume (including the annular volume and reaction vessel 203) of at least 250 milliliters (mL). In some implementations, the reaction vessel 203 has an inner volume of at least 250 mL.

The spill neutralization padding 207 can surround the outer circumferential wall of the housing 201. In some implementations, the spill neutralization padding 207 covers an outer bottom wall of the housing 201. In some implementations, the spill neutralization padding 207 covers the entire outer surface of the housing 201. A ratio of a thickness of the spill neutralization padding 207 to the inner diameter of the reaction vessel 203 can be in a range of about 1:2 to about 8:1. For example, the ratio of the thickness of the spill neutralization padding 207 to the inner diameter of the reaction vessel 203 is about 8:1. The volume or mass of the spill neutralization padding 207 can be sufficient for neutralizing all of the hydrofluoric acid that is disposed within the reaction vessel 203 for transport.

Figure 3:
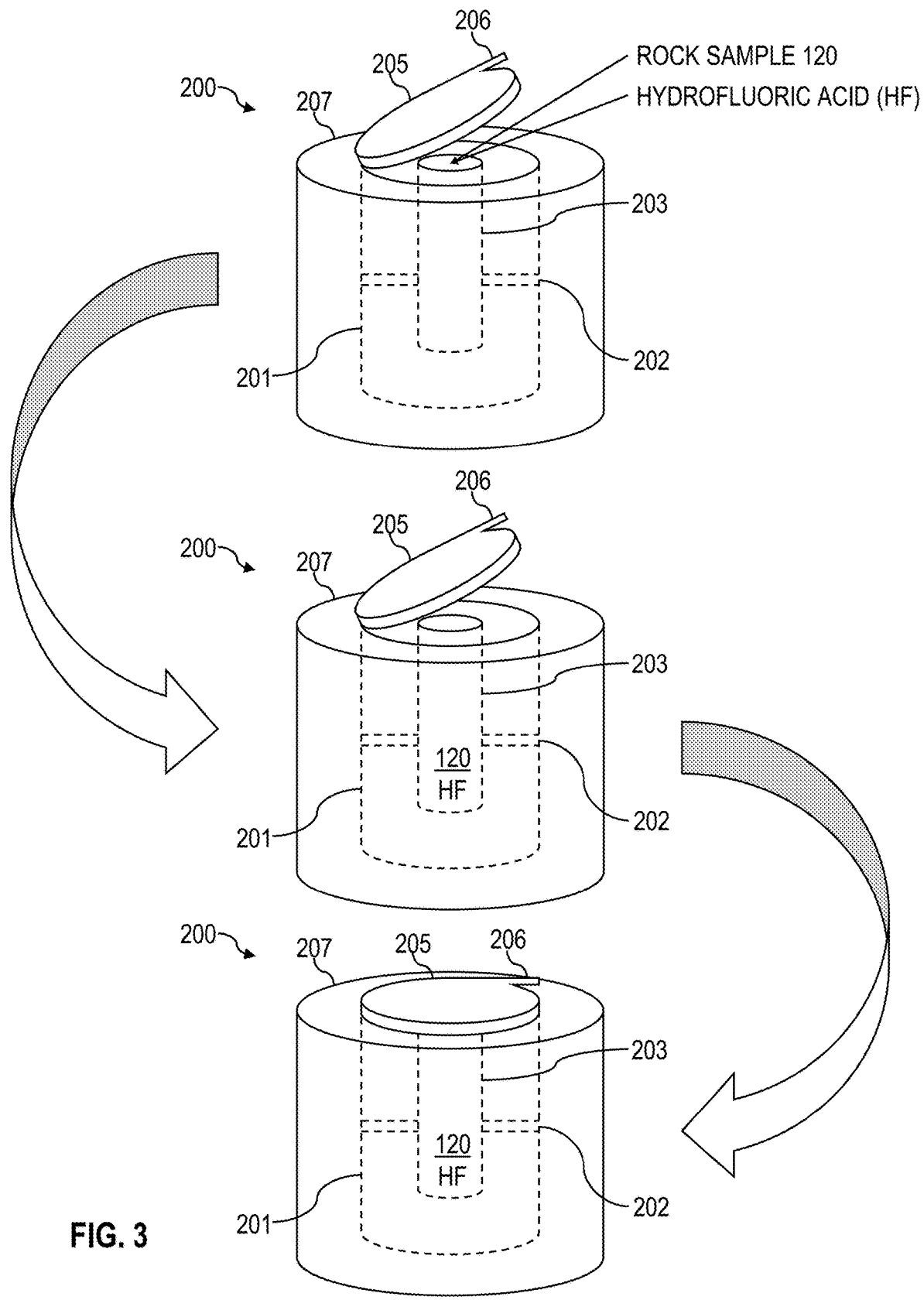
FIG. 3 is an example progression of a rock sample being placed in the apparatus of FIG. 2A.

FIG. 3 is an example progression showing the placement of hydrofluoric acid and a rock sample (such as the rock sample 120) into the apparatus 200. The rock sample 120 and the hydrofluoric acid are placed into the reaction vessel 203 of the apparatus 200, while the lid 205 is in the open position. Once the rock sample 120 and the hydrofluoric acid have been placed into the reaction vessel 203, the lid 205 is switched to the closed position and seals against the housing 201 and the reaction vessel 203, thereby isolating the rock sample 120 and the hydrofluoric acid. The apparatus 200 can then be placed onto a vehicle (such as the vehicle 250) to be transported to another location. In some implementations, multiple implementations of the apparatus 200 (for example, two apparatuses, three apparatuses, four apparatuses, five apparatuses, six apparatuses, or more than six apparatuses) can be placed onto a single vehicle 250. In some cases, each of the apparatuses 200 can store a different rock sample, and each of the apparatuses 200 can be labeled, for example, with source information (such as well number, depth at which the sample was obtained, and core number) and/or sample information (such as sample type and lab maceration number). In such implementations, all of the apparatuses 200 can be transported by the vehicle 250 away from the well site and to a different location, such as a laboratory.

Figure 4:
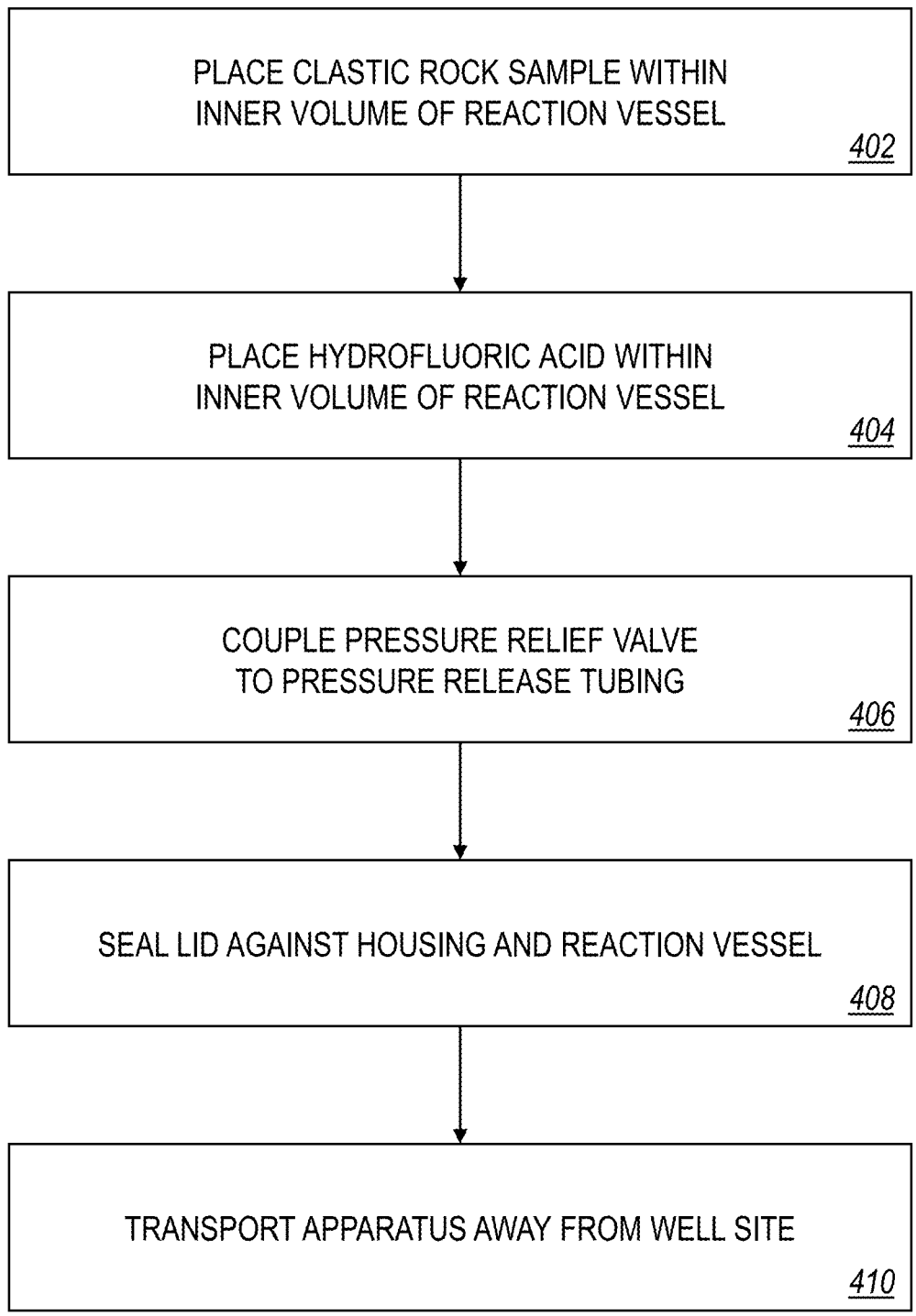
FIG. 4 is a flow chart of an example method for transporting a rock sample.

FIG. 4 is a flow chart of an example method 400 for transporting a clastic rock sample (such as the rock sample 120). The apparatus 200 can be used to implement method 400. At block 402, the rock sample 120 is placed in the apparatus 200 at a well site (such as a well site for the well 100). Placing the rock sample 120 in the apparatus 200 at block 402 includes placing the rock sample 120 within the inner volume of the reaction vessel 203 of the apparatus 200. After placing the rock sample 120 within the inner volume of the reaction vessel 203 at block 402, hydrofluoric acid is placed within the inner volume of the reaction vessel 203 at block 404. At block 406, a pressure relief valve (such as the pressure relief valve 208) is coupled to the pressure release tubing 206. At block 408, the lid 205 is sealed against the housing 201 and the reaction vessel 203, thereby isolating the hydrofluoric acid and the rock sample 120 within the inner volume of the reaction vessel 203. At block 410, the apparatus 200 (with the hydrofluoric acid and the rock sample 120 isolated within the inner volume of the reaction vessel 203) is transported away from the well site. The apparatus 200 can be transported at block 410 using, for example, the vehicle 250. For example, the apparatus 200 can be placed on the vehicle 250, and the vehicle 250 can transport the apparatus 200 away from the well site to a laboratory, where the rock sample 120 can be retrieved and analyzed.

In some implementations, the hydrofluoric acid is in the form of a hydrofluoric acid solution (that is, a mixture of hydrofluoric acid and water). The hydrofluoric acid solution can have a hydrofluoric acid concentration in a range of from about 40% to about 60% or from about 45% to about 55%. For example, a 48% hydrofluoric acid solution can be placed within the inner volume of the reaction vessel 203 at block 404. In some implementations, about 25 milliliters to about 60 milliliters of the hydrofluoric acid solution is placed within the inner volume of the reaction vessel 203 at block 404. For example, about 50 milliliters of the 48% hydrofluoric acid solution is placed within the inner volume of the reaction vessel 203 at block 404.

In some implementations, hydrochloric acid is added to the rock sample 120 prior to placing the rock sample 120 in the inner volume of the reaction vessel 203 at block 402. After the apparatus 200 has been transported away from the well site at block 410 and has arrived at the desired location (for example, a laboratory), the apparatus 200 can be removed from the vehicle 250. The lid 205 can be unsealed from the housing 201 and the reaction vessel 203. For example, the lid 205 can be switched to the open position. The hydrofluoric acid in the apparatus 200 can be removed (for example, decanted). Once the hydrofluoric acid has been removed from the apparatus 200, the rock sample 120 can be neutralized. Neutralizing the rock sample 120 can include a) filling the reaction vessel 203, the housing 201, or both with distilled water; b) allowing the rock sample 120 to rest in the distilled water for a specified resting time duration; c) removing the distilled water from the apparatus 200; and d) repeating in order a), b), and c) until the rock sample 120 has been neutralized. For example, neutralizing the rock sample 120 can include repeating in order a), b), and c) at least two or at least three times. In some implementations, the specified resting time duration is in a range of from about 30 minutes to about 2 hours (for example, about 1 hour). In cases where oil is present in the rock sample 120, the distilled water is replaced with an aqueous detergent solution in neutralizing the rock sample 120. The aqueous detergent solution includes a mixture of a detergent and water. For example, the aqueous detergent solution is a 50/50 mixture of detergent and water. In some cases, oil can be removed from the rock sample 120 by ultrasonic vibrations. In some cases, the rock sample 120 is cleaned by washing with acetone and passing the residue across a vibrating sieve.

After cleaning/neutralizing the rock sample 120, the remaining residue can be sieved. The residue can be passed through a sieve with desired sieve hole dimensions to remove fines of a certain size. For example, a 10 micrometer or 20 micrometer sieve can be used to remove fines that have a maximum dimension of less than 10 micrometers or 20 micrometers, respectively. After sieving, the remaining residue (with fines removed) can be transferred to centrifuge tube(s) and centrifuged at a first specified rotation speed for a first specified centrifuging time duration. In some implementations, the first specified rotation speed is in a range of from 2000 revolutions per minute (rpm) to 5000 rpm. For example, the first specified rotation speed is about 3000 rpm. In some implementations, the first specified centrifuging time duration is in a range of about 1 minute to about 5 minutes. For example, the first specified centrifuging time duration is about three minutes. After centrifuging, the supernatant (liquid) can be removed from the centrifuge tube(s).

Once the supernatant is removed, zinc bromide can be added to the centrifuge tube(s). The zinc bromide can be mixed with the residue in the centrifuge tube(s), for example, using a vortex mixer. Once the zinc bromide has been mixed with the residue in the centrifuge tube(s), the centrifuge tube(s) are once again centrifuged at a second specified rotation speed for a second specified centrifuging time duration. In some implementations, the second specified rotation speed is similar to or the same as the first specified rotation speed. In some implementations, the second specified centrifuging time duration is in a range of from about 5 minutes to about 30 minutes. For example, the second specified centrifuging time duration is about 10 minutes.

The organic residue floating in the supernatant can be transferred to a second centrifuge tube(s). In some cases, organics may be retained in the sink (below the supernatant) with the rock material. In such cases, the sink can be analyzed using a wet mount slide. Hydrochloric acid can be added to the second centrifuge tube(s) including the organic residue. In some cases, only a few drops of concentrated hydrochloric acid is added to the second centrifuge tube(s). The second centrifuge tube(s) are then filled with distilled water. The organic residue can be mixed with the distilled water in the second centrifuge tube(s). Once the organic residue has been mixed with the distilled water in the second centrifuge tube(s), the second centrifuge tube(s) are centrifuged at a third specified rotation speed for a third specified centrifuging time duration. In some implementations, the third specified rotation speed is similar to or the same as the first specified rotation speed. For example, the third specified rotation speed is about 3000 rpm. In some implementations, the third specified centrifuging time duration is similar to or the same as the first specified centrifuging time duration. For example, the third specified centrifuging time duration is about three minutes. After centrifuging, the supernatant is removed from the second centrifuge tube(s). The second centrifuge tube(s) are again filled with distilled water, and the organic residue is again mixed with the distilled water in the second centrifuge tube(s). Once the organic residue has been mixed with the distilled water in the second centrifuge tube(s) a second time, the second centrifuge tube(s) are centrifuged again at the third specified rotation speed for the third specified centrifuging time duration. After centrifuging for the second time, the supernatant is removed from the second centrifuge tube(s).

The remaining organic residue is then evaluated to determine whether there is sufficient residue for oxidation or whether oxidation is needed at all. For example, in some cases, the remaining organic residue contains palynomorphs that are suitable for examination and oxidation is not required for such samples. In some cases, upon visual inspection, it may be determined that the palynomorphs in the remaining organic residue are too dark for accurate identification, and additional oxidation may be required to lighten the color of the palynomorphs. In some cases, additional oxidation may be required to reduce or eliminate amorphous organic contaminants in the remaining organic residue. In some cases, additional oxidation can be performed as a clean-up procedure. The organic residue can be evaluated using wet mount slide(s). If oxidation is needed, the organic residue is sieved (for example, with a 20 micrometer sieve) and a wet mount slide is prepared from the un-oxidized residue.

A portion of the residue is mixed with polyvinyl alcohol (PVA) in a separate tube. A portion of the mixture is then transferred to and distributed across a clean coverslip (for example, a 22 millimeter by 22 millimeter coverslip). The PVA-residue mixture is then allowed to dry, for example, on a slide warming table. After drying, the coverslip is inverted and placed on several drops of an epoxy-based mounting medium with an appropriate refractive index for general petrography (for example, Petropoxy 154), on a clean microscope slide (for example, a 1 inch by 3 inch microscope slide). The slide can be labeled for identification. For example, the slide can be labeled with well information, depth information, sample type information, core number, lab maceration number, or any combination of these. The slide is then dried at a specified drying temperature for a specified drying time duration. In some implementations, the specified drying temperature is in a range of from about 90 degrees Celsius (° C.) to about 110° C. For example, the specified drying temperature is about 100° C. In some implementations, the specified drying time duration is in a range of about 5 minutes to about 20 minutes. For example, the specified drying time duration is at most 20 minutes. After drying, the slide can be evaluated (for example, by using a microscope) to determine the amount and type of oxidation of the organic residue from the rock sample 120.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. An apparatus for transporting a clastic rock sample comprising a palynomorph, the apparatus comprising:
    a housing;
    a reaction vessel disposed within the housing, the reaction vessel configured to hold a specified quantity of hydrofluoric acid and the clastic rock sample;
    a plurality of rods disposed within the housing, each of the rods extending from the housing to the reaction vessel, the plurality of rods securing a position of the reaction vessel within the housing;
    a lid configured to seal against the housing to isolate an annular volume between the housing and the reaction vessel from an external environment, the lid configured to seal against the reaction vessel to isolate an inner volume of the reaction vessel from the external environment;
    a pressure release tubing extending through the lid, the pressure release tubing configured to couple to a pressure relief valve and establish fluid communication between the annular volume and the pressure relief valve once the pressure relief valve is coupled to the pressure release tubing and the lid has sealed against the housing and the reaction vessel; and
    a spill neutralization padding surrounding an external surface of the housing, the spill neutralization padding configured to, in response to coming in contact with the hydrofluoric acid, react with the hydrofluoric acid in an acid-base neutralization reaction.

2. The apparatus of claim 1, wherein the lid is attached to the housing by a hinge, and the hinge is configured to swing the lid between a closed position and an open position, wherein in the open position, the inner volume of the reaction vessel is open for receiving the specified quantity of hydrofluoric acid and the clastic rock sample, and in the closed position, the lid is sealed against the housing and the reaction vessel, thereby isolating the annular volume and the inner volume from the external environment.

3. The apparatus of claim 2, wherein each of the rods extend radially outward from an outer circumferential wall of the reaction vessel to an inner circumferential wall of the housing.

4. The apparatus of claim 3, wherein a volumetric ratio of the annular volume between the housing and the reaction vessel to the inner volume of the reaction vessel is in a range of from 2:1 to 15:1.

5. The apparatus of claim 4, wherein the spill neutralization padding comprises calcium carbonate, and a ratio of a thickness of the spill neutralization padding to an inner diameter of the reaction vessel is about 8:1.

6. A method for transporting a clastic rock sample comprising a palynomorph, the method comprising:
    at a well site, placing the clastic rock sample in an apparatus, the apparatus comprising:
        a housing;
        a reaction vessel disposed within the housing;
        a plurality of rods disposed within the housing, each of the rods extending from the housing to the reaction vessel, the plurality of rods securing a position of the reaction vessel within the housing;
        a lid configured to seal against the housing to isolate an annular volume between the housing and the reaction vessel from an external environment, the lid configured to seal against the reaction vessel to isolate an inner volume of the reaction vessel from the external environment;
a pressure release tubing extending through the lid, the pressure release tubing configured to couple to a pressure relief valve and establish fluid communication between the annular volume and the pressure relief valve once the pressure relief valve is coupled to the pressure release tubing and the lid has sealed against the housing and the reaction vessel; and
a spill neutralization padding surrounding an external surface of the housing, the spill neutralization padding configured to, in response to coming in contact with hydrofluoric acid, reacting with the hydrofluoric acid in an acid-base neutralization reaction, wherein placing the clastic rock sample in the apparatus comprises placing the clastic rock sample within the inner volume of the reaction vessel;
after placing the clastic rock sample within the inner volume of the reaction vessel, placing hydrofluoric acid within the inner volume of the reaction vessel;
coupling the pressure relief valve to the pressure release tubing;
sealing the lid against the housing and the reaction vessel, thereby isolating the hydrofluoric acid and the clastic rock sample within the inner volume of the reaction vessel; and
transporting the apparatus away from the well site.

7. The method of claim 6, wherein transporting the apparatus away from the well site comprises placing the apparatus on an unmanned aerial vehicle (UAV) and causing the UAV to transport the apparatus away from the well site to a laboratory.

8. The method of claim 7, wherein:
the lid is attached to the housing by a hinge;
the hinge allows the lid to swing between a closed position and an open position;
in the open position, the inner volume of the reaction vessel is open for receiving the clastic rock sample and the hydrofluoric acid;
in the closed position, the lid is sealed against the housing and the reaction vessel, thereby isolating the annular volume and the inner volume of the reaction vessel from the external environment; and
the lid is sealed against the housing and the reaction vessel by swinging the lid to the closed position.

9. The method of claim 8, wherein each of the rods extend radially outward from an outer circumferential wall of the reaction vessel to an inner circumferential wall of the housing.

10. The method of claim 9, wherein a volumetric ratio of the annular volume between the housing and the reaction vessel to the inner volume of the reaction vessel is in a range of from 2:1 to 15:1.

11. The method of claim 10, wherein the spill neutralization padding comprises calcium carbonate, and a ratio of a thickness of the spill neutralization padding to an inner diameter of the reaction vessel is about 8:1.

12. The method of claim 11, wherein the clastic rock sample comprises a mixture of rock cuttings and at least a portion of a crushed core sample.

13. The method of claim 12, wherein placing the hydrofluoric acid in the inner volume of the reaction vessel comprises placing about 25 milliliters to about 60 milliliters of a 48% hydrofluoric acid solution in the inner volume of the reaction vessel.

14. The method of claim 13, comprising adding hydrochloric acid to the clastic rock sample prior to placing the clastic rock sample within the inner volume of the reaction vessel.

15. The method of claim 14, comprising, after transporting the apparatus away from the well site:
unsealing the lid from the housing and the reaction vessel;
removing the hydrofluoric acid from the reaction vessel; and
neutralizing the clastic rock sample within the reaction vessel, wherein neutralizing the clastic rock sample comprises:
a) placing distilled water in the reaction vessel;
b) allowing the clastic rock sample to rest in the distilled water for a specified resting time duration;
c) removing the distilled water from the reaction vessel; and
d) repeating in order a), b), and c) at least three times.

16. A system comprising:
a clastic rock sample comprising a palynomorph;
an apparatus for transporting the clastic rock sample, the apparatus configured to be placed on and transported by an unmanned aerial vehicle (UAV), the apparatus comprising:
a housing;
a reaction vessel disposed within the housing, the reaction vessel configured to hold a specified quantity of hydrofluoric acid and the clastic rock sample;
a plurality of rods disposed within the housing, each of the rods extending radially from an outer circumferential wall of the reaction vessel to an inner circumferential wall of the housing, the plurality of rods securing a position of the reaction vessel within the housing;
a lid configured to seal against the housing to isolate an annular volume between the housing and the reaction vessel from an external environment, the lid configured to seal against the reaction vessel to isolate an inner volume of the reaction vessel from the external environment;
a hinge attaching the lid to the housing, the hinge configured to swing the lid between a closed position and an open position, wherein in the open position, the inner volume of the reaction vessel is open for receiving the specified quantity of hydrofluoric acid and the clastic rock sample, and in the closed position, the lid is sealed against the housing and the reaction vessel, thereby isolating the annular volume and the inner volume from the external environment;
a pressure release tubing extending through the lid;
a pressure relief valve coupled to the pressure release tubing, wherein the pressure release tubing is configured to establish fluid communication between the annular volume and the pressure relief valve once the pressure relief valve is coupled to the pressure release tubing and the lid has sealed against the housing and the reaction vessel, and the pressure relief valve is configured to relieve pressure from the annular volume once a pressure within the annular volume has reached a maximum threshold pressure value; and
a spill neutralization padding surrounding an external surface of the housing, the spill neutralization padding configured to, in response to coming in contact with the hydrofluoric acid, reacting with the hydrofluoric acid in an acid-base neutralization reaction.

17. The system of claim 16, wherein a volumetric ratio of the annular volume between the housing and the reaction vessel to the inner volume of the reaction vessel is in a range of from 2:1 to 15:1.

18. The system of claim 17, wherein the spill neutralization padding comprises calcium carbonate, and a ratio of a thickness of the spill neutralization padding to an inner diameter of the reaction vessel is about 8:1.

19. The system of claim 18, wherein the clastic rock sample comprises a mixture of rock cuttings and at least a portion of a crushed core sample.

* * * * *